United States Patent [19]

Ellis

[11] Patent Number: 4,527,565

[45] Date of Patent: Jul. 9, 1985

[54] COLD FACIAL APPLICATOR

[76] Inventor: Billie J. Ellis, 9017 Finney Point Dr., Ooltewah, Tenn. 37363

[21] Appl. No.: 583,989

[22] Filed: Feb. 27, 1984

[51] Int. Cl.³ .............................................. A61F 7/10
[52] U.S. Cl. ..................................... 128/402; 128/403
[58] Field of Search ............... 128/380, 399, 402, 403; 132/88.5

[56] References Cited

U.S. PATENT DOCUMENTS

| | | | |
|---|---|---|---|
| 1,480,780 | 1/1924 | Pauley | 128/402 |
| 2,477,883 | 8/1949 | Lefohn | 128/402 |
| 3,545,230 | 12/1970 | Morse | 128/403 X |
| 3,736,769 | 6/1973 | Petersen | 128/402 X |
| 3,868,984 | 3/1975 | Jorgensen | 128/403 X |
| 3,885,403 | 5/1975 | Spencer | 128/399 X |

*Primary Examiner*—Anton O. Oechsle

*Attorney, Agent, or Firm*—Alan Ruderman

[57] ABSTRACT

A cold facial compress in the form of a mask has two sheets of flexible material bonded together along common edges and contains a gel in the space formed therebetween. The compress including the gel remains pliable at temperatures below that at which water freezes and may be maintained in the freezer section of a refrigerator and thereafter applied to the face of the user. The mask includes a notch adapted to be disposed beneath and about the nose of the user, an elongated opening adopted to be positioned about the lips of the user and a sharp notch disposed beneath the nose receiving notch and the slot. The mask is symmetrical about a line extending through the central portion of the notches and the slot and has a shape such as to be used by persons having faces of various sizes and shapes.

13 Claims, 3 Drawing Figures

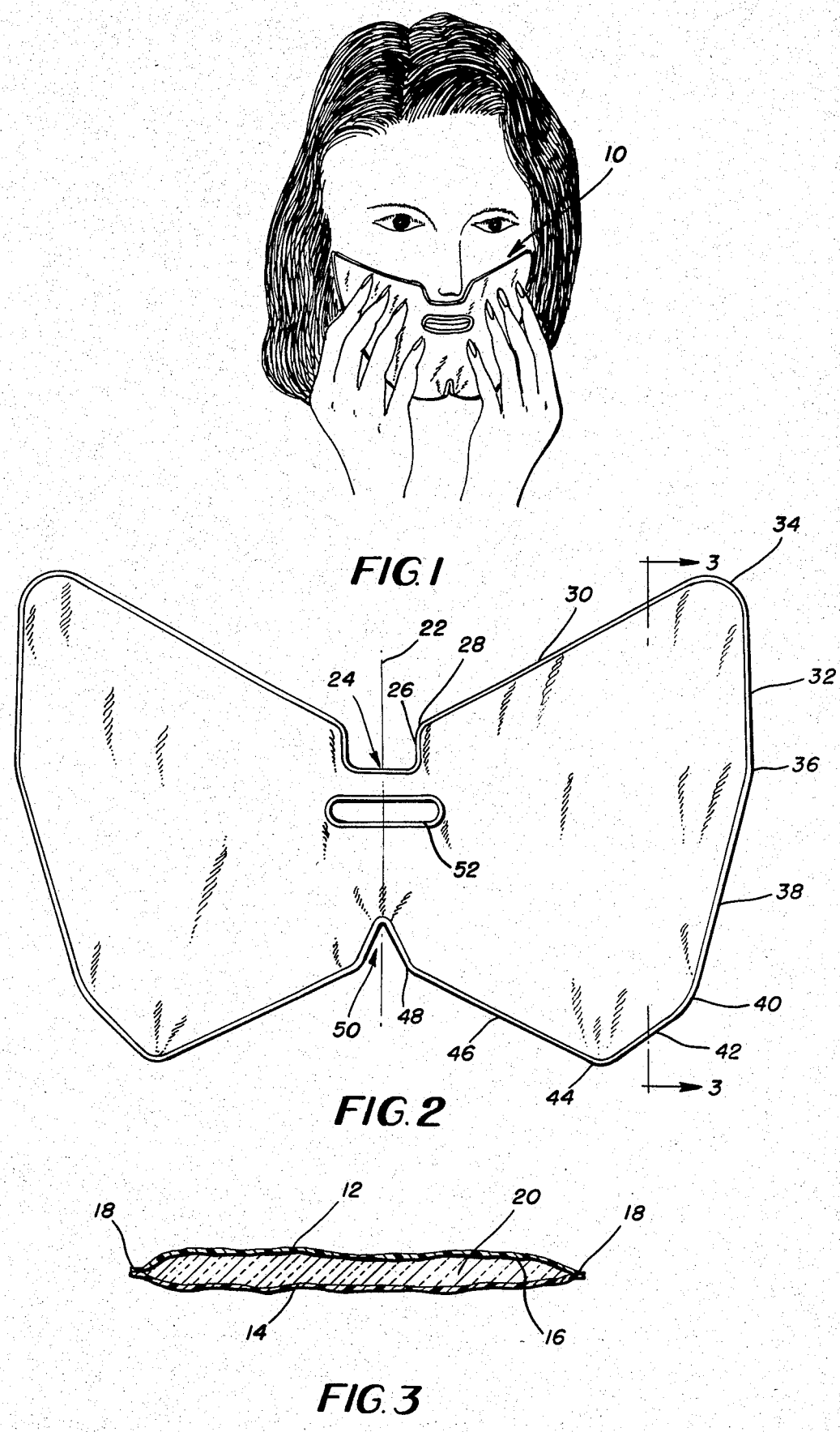

COLD FACIAL APPLICATOR

BACKGROUND OF THE INVENTION

This invention relates generally to cosmetics and more particularly to a cold facial compress which may be used by applying to the face of a person for effecting contraction of the facial and neck tissue, the compress having a configuration permitting use by persons having various size faces and containing a coolant material which remains pliable when subjected to low temperatures and is slow to absorb heat.

The application of cold toweling and the like have been used by beauty salons and other cosmetologists for the purpose of shrinking and contracting the facial tissues, such use over long periods of time having the effect of preventing wrinkling of the facial skin tissue. When using toweling wetted and cooled in a refrigerator or the like the toweling rapidly absorbs heat and must be recooled repeatedly. As the toweling absorbs heat the frozen water melts and is uncomfortable to the user. Moreover, the toweling covers substantially the entire face or at least the mouth and nose of the user. Although there have been various cooling packages proposed for therapeutic purposes no facial applicator having slow heat absorbtion capabilities are known to have been proposed in the prior art. For example, Paul U.S. Pat. No. 4,243,041 proposed goggles for use about the eyes and nose of a user subsequent to surgery; Brennen U.S. Pat. No. 4,190,054 proposed a wrap positionable about the head and neck; and Salem U.S. Pat. No. 4,092,982 proposed an elongated wrap for use about a foot or the like. Furthermore, a facial mask type wet heated toweling positioned about the cheeks and chin of the facial area of a user has been proposed for softening facial wiskers prior to shaving as illustrated in Dopyera U.S. Pat. No. 2,082,153.

SUMMARY OF THE INVENTION

Consequently, it is a primary object of the present invention to provide a cold facial applicator in the form of a mask which contains a coolant and has a configuration which permits universal use for persons of varying size faces.

It is another object of the present invention to provide a cold facial pack having flexible sheet material spaced apart and containing therebetween a material which remains pliable when cooled to refrigeration temperatures which would freeze water and is slow to absorb heat, the pack having a configuration which permits use about the lower portion of the face of a user from the cheekbone and extending toward and including the neck, portions of the pack overlapping along the neck for use by persons having faces of varying sizes and shapes.

Accordingly, the present invention provides a cold facial compress in the form of a mask comprising two sheets of flexible material bonded together along common edges and containing in the space formed between the sheets a gel which remains pliable at temperatures below that at which water freezes so that the mask may be maintained in the freezer section of a refrigerator and when applied to the face of a user may flexibly conform to the face, the cold surface causing the facial tissues to contract.

The shape of the mask is such that it will be disposed on the face of the user extending from the cheek bone at the top edges along the jawbone adjacent and below the ear, and extending along the neck beneath the jawbone and beneath the chin. The mask is symmetrical about a central vertically extending line, and an open ended recess at the upper central portion is disposed beneath the nose of the user and a slot is spaced beneath the recess to provide an opening over the lips of the user. At the lower portion of the symmetrical center line the mask smoothly tapers away from a notch toward each side, and when in use these edges overlap, the degree of overlapping depending upon the size of the face of the user.

BRIEF DESCRIPTION OF THE DRAWINGS

The particular features and advantages of the invention as well as other objects will become apparent from the following description taken in connection with the accompanying drawings, in which:

FIG. 1 is a perspective view illustrating a cold facial compress mask constructed in accordance with the principles of the present invention typically as it would be used;

FIG. 2 is an elevational view of the mask illustrated in FIG. 1 in the fully open extended position; and FIG. 3 is a cross-sectional view taken substantially along line 3—3 of FIG. 2.

DESCRIPTION OF THE PREFERRED EMBODIMENT

Referring now to the drawings, a cold facial compress constructed in accordance with the principles of the present invention is in the form of a mask 10 comprising a pair of spaced sheets of flexible material 12 and 14 respectively, the material being a synthetic flexible plastic preferably vinyl. Both sheets are of the same size and shape and are bonded together along all the common edges by heat staking or the like to form a sealed interior cavity 16, disposed between the sheets 12, 14. Generally the sheets will be bonded together to form a seal about the common edges such as at 18 while leaving a small portion thereof open for filling the interior cavity with a gel 20, and once filled the remaining portions of the sheets are sealed. The gel 20 may be any substance which retains its pliable characteristics when maintained for extensive periods in a refrigerator and particularly the freezer portion of the refrigerator, and which acts as a coolant in that it absorbs heat slowly. A gel which meets these requirements comprises a mixture of water, glycol and cylicate gel which may be mixed in varying proportions to provide a gel which is pliable below the freezing temperature of water. One such gel is sold by the Chattanooga Corporation in a product under the name COL PAC. Another material is produced by 3M Company and marketed under the name CRYOGEL.

As best illustrated in FIG. 2 each of the sheets 12, 14 has the general configuration of a butterfly, being substantially symmetrical about a center line 22. A substantially rectangular nose receiving notch 24 is formed in the upper edge substantially intermediate the width of the mask and, from each side edge 26 of the notch, from a point 28 the upper edge 30 extends outwardly at an acute angle to the center line toward the outer edges 32, the transition from the upper edge 30 to the outer edge preferably being a smooth arcuate contour 34. When in use the nose of the user is positioned within the notch 24 and the upper edge 30 extends along the cheekbone to the temple at the junction 34 from whence the edge 32 extends downwardly adjacent and below the ear of the user along the upper part of the jawbone. The edge 32 preferably at a transition point 36 thereafter tapers slightly back toward the center line 22 along an edge 38 which extends beneath the jawbone along the neck of the user. Again the outer edge transitions at 40 from the edge 38 angling back along an edge 42 further toward the center line 22, the edges 42 being folded back toward each other when used as a compress so as to tuck together beneath the jawbone and about the neck of the user. From the edges 42 the sheets extend sharply back from a lower transition point 44 along an edge 46 which extends about the neck and beneath the chin of the user. The edge 46 transitions back preferably at a transition point 48 sharply toward the center line 22 to form a sharp narrow notch 50 symmetrical about the center line and about which the mask may be folded. Depending upon the size of the user's face the edges 46 more or less overlap one another in use as do the edges of the notch 50 from the point 48 to the apex of the notch 50.

Disposed symmetrically in the mask beneath the nose receiving notch 24 and above the sharp narrow notch 50 is a laterally elongated slot 52 forming an aperture which extends about the lips of the user, the border of the slot 52 being sealed by heat staking or the like as aforesaid.

The mask is generally maintained in the freezer compartment of the refrigerator and becomes cold. When used it is removed and placed about the face of the user as illustrated in FIG. 1 with the slot 52 disposed about the lips of the user and the notch 24 beneath the nose. The fingers of the user hold the mask against the face while the thumbs manipulate the portions along edges 42 through 46 about the neck and chin to engage all the skin tissue areas. Because of the shape of the edges 38 through 46 and the notch 50, the mask may be folded about these areas of persons having varying size faces, so that a single size may be universally utilized.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A cold facial compress in the form of a mask for applying to the face of a person, said compress comprising two layers of flexible sheet material sealed about their peripheries to form a cavity, a coolant gel disposed in said cavity, said gel having the property of remaining pliable when cooled in the freezer compartment of a refrigerator, said sheet materials each having a peripheral configuration including a wide notch for disposition beneath and about the nose of the person, and a sharp notch spaced below said wide notch, said sheets being substantially symmetrical about a line extending through said notches, an upper edge extending upwardly from an edge at each side of said wide notch at an angular disposition to said line for extending substantially along the cheekbone of said person and terminating at a temple engaging edge, a side edge extending from said temple engaging edge and downwardly to a lowermost edge for tucking beneath the person's jawbone, a neck engaging edge extending upwardly to said sharp notch at an angular disposition to said line, and an opening disposed intermediate said notches to define an aperture about the lips of said person, the peripheral border of the sheet material definining said opening being sealed about the periphery.

2. A cold facial compress as recited in claim 1, wherein said side edge comprises a first downwardly extending portion, a second portion extending downwardly at an angular disposition toward said line, and a third portion extending downwardly from said second portion at a sharper angle toward said line.

3. A cold facial compress as recited in claim 2, wherein said neck engaging edges at opposite sides of said line fold about said line, whereby one of said edges may overlap the compress at the other side of said line and conform to persons having faces differing in size.

4. A cold facial compress as recited in claim 3, wherein said gel comprises water, glycol and silicate gel.

5. A cold facial compress as recited in claim 3, wherein said sheet material is vinyl.

6. A cold facial compress as recited in claim 2, wherein said compress is foldable through said notches about said line for superposing a portion of the material on one side of said line upon that of the other side of said line.

7. A cold facial compress as recited in claim 6, wherein said gel comprises water, glycol and silicate gel.

8. A cold facial compress as recited in claim 6, wherein said sheet material is vinyl.

9. A cold facial compress as recited in claim 2, wherein said first portions extend along the base of the persons adjacent the ears, said second portions extend along and beneath the jawbone, and said third portions engage the neck beneath the jawbone.

10. A cold facial compress as recited in claim 9, wherein said neck engaging portion engages the neck beneath the chin.

11. A cold facial compress as recited in claim 9, wherein said compress is foldable through said notches about said line for superposing a portion of the material on one side of said line upon that of the other side of said line.

12. A cold facial compress as recited in claim 11, wherein said gel comprises water, glycol and silicate gel.

13. A cold facial compress as recited in claim 11, wherein said sheet material is vinyl.

* * * * *